United States Patent
West

(10) Patent No.: US 6,537,525 B1
(45) Date of Patent: Mar. 25, 2003

(54) MEDICATED CHEWING-GUM

(76) Inventor: Douglas H. West, 2760 N. Liberty Keuter Rd., P.O. Box 91, Lebanon, OH (US) 45036

( * ) Notice: Subject to any disclaimer, the term of this patent is extended or adjusted under 35 U.S.C. 154(b) by 970 days.

(21) Appl. No.: 08/790,528

(22) Filed: Jan. 29, 1997

(51) Int. Cl.$^7$ .............................. A61K 7/16; A61K 9/68
(52) U.S. Cl. ...................... 424/48; 424/440; 424/441; 424/634; 514/399; 514/406
(58) Field of Search .................... 424/48, 440, 441, 424/634; 514/399, 406

(56) References Cited

U.S. PATENT DOCUMENTS

| | | | | |
|---|---|---|---|---|
| 4,139,589 A | * | 2/1979 | Beringer et al. | 264/260 |
| 4,647,450 A | * | 3/1987 | Peters | 424/48 |
| 4,971,787 A | * | 11/1990 | Cherukuri | 424/48 |
| 5,294,433 A | | 3/1994 | Singer et al. | 424/52 |
| 5,364,616 A | | 11/1994 | Singer et al. | 424/52 |
| 5,552,163 A | | 9/1996 | Hartman et al. | 426/3 |
| 5,562,936 A | | 10/1996 | Song et al. | 426/3 |
| 5,567,450 A | | 10/1996 | Zuromski et al. | 426/5 |
| 5,599,577 A | | 2/1997 | Stevens et al. | 427/2.14 |

FOREIGN PATENT DOCUMENTS

| | | | |
|---|---|---|---|
| EP | 322 048 | * | 6/1992 |
| EP | 349 103 | * | 11/1992 |
| WO | 92/17161 | * | 10/1992 |
| WO | 95/05173 | * | 2/1995 |

OTHER PUBLICATIONS

Drug Facts and Comparisons 1996 Wolters Kluwer, St. Louis. Chapter 7, p 1824–1891, Jan. 1996.*
Physician's Desk Reference for Non Prescription Drugs 17th ed. 1996 p. 799.
Consumer's Digest Mar./Apr. 1997 p. 71.
Abstracts of Papers, May 1980, p. 1181
Archs oral Biol. vol. 38, No. 10, pp. 885–891, 1993.
Archs oral Biol. vol. 40, No. 8, pp. 699–705, 1995.
Caries Res 1992;26:176–182.
Abstract, Pharm. Res. 1992 Feb. 9(2), p. 255–9.
Abstract, Caries Res. 1992 26(3), p. 176–82.
*Environmental Nutrition*, Nov. 1995 v18 n11 p. 3(1).
Facts on file, Dec. 21, 1995, p. 957.
*FDA Consumer*, 1995 (remainder of citation unknown).
Gastroenterology 75: 275–77, 1978.
Gastroenterology 1981; 81:376–94.
Gastroenterology, vol. 108, No. 4, p. A204.
Harrison's Principles of Internal Medicine, Chap. 314, p. 1447–48.
*HealthFacts*, Jun. 1995 v20 n193, p. 2(1).
Industry Week, Jan. 8, 1996 v245, p. 14.
J. Clin. Invest 65: 256–267 (Feb. 1980).
Pharmaceutical Research, vol. 9, No. 2, pp. 255–259, 1992.
Pharmazie 1992 47 (8):607–9.
*Physician's Desk Reference*, 50th ed. 1996:529–30, 2562–63.
Scand J. Dent Res. 1993: 101: 386–390.
*Bockus Gastroenterology*, 5th ed. 1995, Chapter 34.

* cited by examiner

Primary Examiner—Mary K. Zeman
(74) Attorney, Agent, or Firm—Killworth, Gottman, Hagan & Schaeff, L.L.P

(57) ABSTRACT

The present invention is directed to chewing-gum preparations which are particularly useful for treating gastroesophageal reflux disease. Typically, the chewing-gum preparation comprises a chewing-gum base and more than one ingredient selected from the group consisting of an acid neutralizing agent, an anti-gas agent, and an acid production inhibitor, and desirably all three ingredients. The invention is also directed to a method for treating gastroesophageal reflux disease comprising the step of masticating a chewing-gum preparation including a gum base and more than one ingredient selected from the group consisting of an acid neutralizing agent, an anti-gas agent, and an acid production inhibitor, and desirably all three ingredients.

20 Claims, No Drawings

MEDICATED CHEWING-GUM

BACKGROUND OF THE INVENTION

One of the most common gastrointestinal ailments to afflict modern man is gastroesophageal reflux disease (GERD). GERD includes such symptoms as heartburn, indigestion, sour stomach, dyspepsia and flatulent dyspepsia. The frequency of the occurrences of GERD is difficult to estimate, but it is reasonable to assume that a majority of individuals living in industrialized societies today suffer from it at one time or another. Dietary indiscretion appears on the surface to be the primary cause along with stress, but GERD actually has a multifactorial etiology. The extent of the problem is evidenced by the multitude of prescription and non-prescription remedies available to the sufferer and the billions of dollars spent annually on treatments for GERD.

Multiple factors contribute to the occurrence of GERD. These factors include: efficacy of the anti-reflux mechanism; volume of gastric fluid; potency of the refluxed material; efficiency of esophageal clearance; and tissue resistance of the esophageal mucosa. The extent and severity of reflux esophagitis depends not on gastroesophageal reflux alone, but also upon the volume of gastric juice available to reflux, the potency of the refluxed material, the interval that the refluxed material remains in the esophagus, and the ability of the esophageal tissue to withstand injury and to repair itself after injury.

Currently, treatments available over the counter, i.e. without a prescription from a physician, include antacid preparations, anti-gas preparations, combination antacid and anti-gas preparations, and bismuth containing compounds. More recently, histamine H-2 receptor antagonists, which are now available over the counter, and proton pump inhibitors, which are not currently available over the counter, have added substantially to the treatment armamentarium. However, none of these preparations addresses the multifactorial etiology of gastroesophageal reflux disease. Thus, a need has developed in the art for a composition for the treatment of GERD which addresses that multifactorial etiology.

SUMMARY OF THE INVENTION

The present invention provides a composition and method for the treatment of GERD which address the multifactorial etiology of GERD. The composition and method of the present invention address all five of the etiologic factors of GERD in a potentiating way which can not be accomplished when the various ingredients of the composition are used individually.

One embodiment of the invention is directed to a masticatory for treating gastroesophageal reflux disease. The masticatory includes more than one ingredient selected from the group consisting of an acid neutralizing agent, an anti-gas agent, and an acid production inhibitor; and a chewing-gum base. Desirably, the masticatory contains all three ingredients with the gum. The masticatory desirably comprises, by weight percent of the total composition, from about 1 wt. % to about 50 wt. % of the acid neutralizing agent; from about 0.1 wt. % to about 15 wt. % of the anti-gas agent; from about 0.001 wt. % to about 65 wt. % of the acid production inhibitor; and from about 20 wt. % to about 98 wt. % of the chewing-gum base.

Another embodiment of the invention is directed to a chewing-gum composition for the treatment of gastroesophageal reflux disease. The chewing-gum composition includes a chewing-gum integral with a chewable tablet. The chewable tablet. includes more than one ingredient selected from the group consisting of an acid neutralizing agent, an anti-gas agent, and an acid production inhibitor. Desirably, the chewable tablet contains all three ingredients. In one instance, the chewing-gum is contained in the chewable tablet. In another instance, the chewable tablet is contained in the chewing-gum.

The present invention is also directed to a method for treating gastroesophageal reflux disease. The method comprises the step of masticating a chewing-gum preparation including a gum base and more than one ingredient selected from the group consisting of an acid neutralizing agent, an anti-gas agent, and an acid production inhibitor. Desirably, all three, namely, an acid neutralizing agent, an anti-gas agent, and an acid production inhibitor are formed into a chewable tablet which is encased in the chewing-gum base.

DETAILED DESCRIPTION OF THE INVENTION

As stated above, the present invention includes chewing-gum compositions and a method employing a chewing-gum composition for treating gastroesophageal reflux disease, which includes symptoms such as, but is not limited to, heartburn, indigestion, sour stomach, dyspepsia and flatulent dyspepsia. Medicated chewing-gum is a unique means of drug delivery in the pharmaceutical industry. Unlike the traditional dosage forms, such as liquids or pills, the medicated chewing-gum of the present invention is a masticatory, i.e., it is intended to be chewed for a period of time, desirably for 20–30 minutes, and then the remaining mass of gum base is intended to be discarded. During the chewing process, most of the medications contained within the gum product are released into the saliva and are either absorbed through the buccal mucosa or swallowed and absorbed through the gastrointestinal tract. The medicated chewing-gum of this invention includes more than one ingredient selected from the group consisting of an acid neutralizing agent, an anti-gas agent, an acid production inhibitor, and desirably all three ingredients, and a chewing-gum base.

The acid neutralizing agent possesses a straightforward mechanism of action. Acid neutralizing agents, such as non-absorbable antacids, combine with hydrochloric acid in the esophagus and stomach neutralizing it. The acid neutralizing agent raises the gastric pH above 5 so that the proteolytic capacity of digestive enzymes, such as pepsin, is reduced and the damaging effect due to acidity is minimized. Some antacids also inactivate pepsin by an adsorbent effect.

The anti-gas agent relieves flatulence by a defoaming and dispersing action to prevent the formation of mucus-surrounded gas pockets in the gastrointestinal tract. The use of an anti-gas substance thus addresses the increased gastric volume that can contribute to GERD.

The acid production inhibitor, along with the antacid, elevates the pH of the stomach contents and consequently any materials refluxed into the esophagus. The acid production inhibitor treats two of the five factors which contribute to GERD by decreasing gastric volume and by decreasing the acidity of the gastric fluid. For example, H-2 receptor antagonists competitively inhibit histamine H-2 receptors. Both the acid concentration and gastric volume of secretion is suppressed proportional to the volume output by the H-2 receptor antagonist. As another example, proton pump inhibitors act to prevent the formation of stomach acid resulting in an increased gastric pH level.

With this invention, it is possible to mix and match those three ingredients for the effect desired. For example, an antacid/anti-gas mixture may be used, or an acid production inhibitor/antacid mixture, etc. As long as a combination of ingredients is used with a chewing-gum base, the multifactorial approach of the present invention is satisfied.

Chewing-gum, itself, treats four of the five factors contributing to GERD. First, chewing gum stimulates salivary secretion and bicarbonate production is the final product of salivary stimulation. The mechanisms capable of increasing esophageal pH after entry of acid fluid into the esophagus include the following: dilution of the fluid; acid neutralization; back diffusion of hydrogen ions across the esophageal mucosa; and complete clearing of the acid volume. Under basal conditions, saliva has a pH of 6–7. During stimulated flow of salivary fluids, salivary pH and capacity to neutralize acid increase. The dilutional and buffering effects of bicarbonate neutralize acidic esophageal contents. Second, chewing gum increases esophageal peristalsis by stimulating deglutition. Evidence suggests that primary peristalsis (swallowing) is the main type of esophageal motor activity that clears the esophagus of refluxed acid in normal subjects. Stimulating salivary flow by chewing gum has been shown to significantly decrease esophageal acid contact time in symptomatic patients. In one study, 70% of the patients exhibiting symptoms of heartburn reported decreased heartburn during salivary stimulation. Third, chewing gum is an activity that rarely takes place in a recumbent posture. When gum is chewed by a person in an upright position, gravity helps propel esophageal contents distally. Gravity, peristalsis, and saliva all contribute to the normal esophageal clearance. A few peristaltic sequences rapidly empty 90–95% of acid fluid from the esophagus. By decreasing the acid contact time by chewing gum, esophageal permeability may also be decreased.

The various active ingredients, i.e. the anti-gas agent, the acid production inhibitor and the acid neutralizing agent are present in the compositions of this invention in safe and useful amounts. "Safe and useful amount", as used herein, means an amount of a substance large enough to provide a significant positive modification of the condition to be treated, but small enough to avoid serious side effects (at a reasonable benefit/risk ratio), within the scope of sound medical judgment. A safe and useful amount of the ingredient will vary with the particular condition being treated, the severity of the condition, the duration of the treatment, the nature of concurrent therapy, and like factors.

The ingredients of the compositions of this invention are also compatible. The term "compatible" as used herein, means that the ingredients of the compositions are capable of being commingled with one another, in a manner such that there is no interaction which would substantially reduce the efficacy of the chewing-gum composition under ordinary use conditions.

Useful antacids are selected from the group consisting of calcium carbonate, magnesium oxide, magnesium hydroxide, magnesium trisilicate, magnesium carbonate, aluminum hydroxide and mixtures thereof. Desirably, the antacid will be calcium carbonate and magnesium hydroxide because its neutralizing action is prolonged and it reduces peptic activity. Magnesium oxide is 8 to 10 times more potent than magnesium trisilicate or magnesium carbonate. The constipating effect of calcium carbonate can be offset by combining it with magnesium oxide, if the two are used in combination. Desirably, the acid neutralizing agent will be used in an amount from about 1 wt. % to about 50 wt. % of the total composition and will more desirably be from about 11 wt. % to about 22 wt. % of the total composition.

The anti-gas agent can be any agent currently used to reduce flatulence by dispersing and preventing the formation of mucus-surrounded gas pockets in the gastrointestinal tract. Desirably, the anti-gas agent will be simethicone. Desirably, the anti-gas agent will be used in an amount from about 0.01 wt. % to about 15 wt. % of the total composition and more desirably from about 1.5 wt. % to about 3.5 wt. % of the total composition.

Useful acid production inhibitors are selected from the group consisting of H-2 receptor antagonists, proton pump inhibitors, their hydrochloride salts, and mixtures thereof. H-2 receptor antagonists are extensively used as drugs for preventing release of acid in the stomach to promote the healing of peptic ulcers and to relieve symptoms of esophagitis and GERD. Proton pump inhibitors suppress gastric acid secretion by specific inhibition of the $H^+/K^+$ ATPase enzyme system at the surface of the gastric parietal cell. By inhibiting this particular enzyme system, the proton pump inhibitor effectively blocks the final stage of acid production.

Useful H-2 receptor antagonists are any H-2 receptor antagonists currently in use in the art. The only requirement is that the H-2 receptor antagonist be compatible with the other medications employed in the compositions of this invention.

Desirably, the H-2 receptor antagonist will be cimetidine (SKF-92334) which is technically known as N-cyano-N'-methyl-N''-(2-(((5-methyl-1-H-imidazol-4-yl)methyl)thio) guanidine. It is disclosed in the *Merck Index*, 11th Ed. (1989) at 354 (entry no. 2279), and the *Physicians' Desk Reference*, 46th Ed. (1992) at 2228. Related useful H-2 receptor antagonists include burimamide and metiamide.

Other desirable H-2 receptor antagonists are ranitidine and, especially, its hydrochloride salt (AH-19065). Ranitidine is N-(2-(((5-((dimethylamino)-methyl)-2-furanyl) methyl)thio)ethyl)-N'-methyl-2-nitro-1,1-ethenediamine. It is disclosed in the *Merck Index*, 11th Ed. (1989) at 1291 (entry no. 8126), and the *Physicians' Desk Reference*, 46th Ed. (1992) at 1063. Related useful compounds include hydroxymethyl ranitidine; ranitidine bismuth citrate (GR-122311, GR-122311X); and AH-18801, N-cyano-N'-(2-(((5-((dimethylamino)methyl)-2-furanyl)methyl)thio)ethyl)-N''-methyl guanidine.

Another desirable H-2 receptor antagonist is famotidine (YM-1170, MK-208) which is technically known as 3-(((2-((aminoiminomethyl)amino)A-thiazolyl)methyl)thio)-N-aminosulfonyl) propanimidamine. Famotidine is disclosed in the *Merck Index*, 11th Ed. (1989) at 617 (entry no. 3881), and the *Physicians' Desk Reference*, 46th Ed. (1992) at 1524. Famotidine is the desirable H-2 receptor antagonist because it has been statistically shown to be significantly more effective than placebo or ranitidine in the healing of esophageal lesions associated with heartburn.

Still another desirable H-2 receptor antagonist is nizatidine (LY-139037, ZL-101) which is known technically as N-(2-(((2-((dimethylamino)methy)-4-thiazolyl)methyl)thio) ethyl)-N'-methyl-2-nitro-1,1-ethanediamine. Nizatidine is disclosed in the *Merck Index*, 11th Ed. (1989) at 1052 (entry no. 6582), and the *Physicians' Desk Reference*, 46th Ed. (1992) at 1246.

One desirable proton pump inhibitor is lansoprazole. Lansoprazole is a substituted benzimidazole technically known as 2-[[[3-methyl-4-(2,2,2-trifluroethoxy)-2-pyridyl] methyl]sulfinyl]benzimidazole. Lansoprazole is disclosed in the *Physicians' Desk Reference*, 50th Ed. (1996) at 2562.

Another desirable proton pump inhibitor is omeprazole which is also a substituted benzimidazole and is technically known as 5-methoxy-2-[[(4-methoxy-3,5-dimethyl-2-pyridinyl)methyl]sulfinyl]-1-H-benzimidazole. Omeprazole is disclosed in the *Merck Index*, 11th Ed. (1989) at 6799 (entry no. 6800), and the *Physicians' Desk Reference*, 50th Ed. (1996) at 529.

The compositions of the present invention include a safe and useful amount of the acid production inhibitor. Desirably, the compositions will include from about 0.001 wt. % to about 65 wt. % of the total composition, more desirably from about 0.007 wt. % to about 40 wt. % of the total composition and most desirably from about 0.2 wt. % to about 31 wt. % of the total composition of the acid production inhibitor.

The chewing-gum base will constitute from about 20 wt. % to about 98 wt. % of the total composition. It has been determined that the size of the chewing-gum base affects salivary flow rates with a normal 3 g size producing less flow than a 9 g size which is near maximal chewable size. The chewing-gum base in the compositions of the present invention has a mass from about 1 g to about 10 g and desirably from about 1.5 g to about 5 g.

The chewing-gum compositions of the present invention may also include additional ingredients, such as, for example, surfactants, flavoring agents, sweetening agents, binders, humectants, thickening agents, buffering agents, preservatives, coloring agents and pigments, and water.

Because some acid production inhibitors have limited water solubility, they may be poorly released from a chewing-gum base. To increase the solubility of the acid production inhibitors and any other ingredient which may require an additional agent to increase its solubility, the compositions of the present invention may include a surfactant. Surfactants useful to increase the solubility of any of the various ingredients of the compositions of this invention include polysorbates, poloxamers and lipophilic anionic surfactants. Surfactants are generally present in the compositions of the present invention in an amount from 0.1 wt. % to about 10 wt. % of the total composition and desirably from about 0.2 wt. % to about 5 wt. % of the total composition.

Water is an optional ingredient of the compositions of the present invention. Water employed in the compositions should desirably be of low ion content and free of organic impurities.

Flavoring agents are also desirable in the chewing-gum compositions of the present invention in order to make them more palatable and to increase salivary flow rates. As stated above, the act of chewing gum causes asymmetric mechanical stimulation from one side of the mouth that elicits high salivary flow responses. Chewing-gums containing a flavoring agent, such as cinnamon or organic acids, stimulate even higher salivary flow than other flavoring agents. The highest pH in saliva was elicited with cinnamon flavored gum with a pH of 7.5 lasting nearly 20 minutes and flow peaking at around 12 times unstimulated flows and falling to nearly 3 times the unstimulated rate at 20 minutes. Peppermint showed no advantage over other flavors and may disadvantageously relax lower esophageal sphincter pressure. Useful flavoring agents are selected from the group consisting of menthol, organic acids, oil of cinnamon, oil of wintergreen, oil of peppermint, oil of spearmint, oil of sassafras, oil of clove and other commonly used flavoring agents. One skilled in the art will appreciate that any flavoring agent currently used in the art to flavor chewing-gums may be used in the compositions of this invention. Desirably, the flavoring agent will be an organic acid, such as citric acid, or oil of cinnamon. If present, flavoring agents are generally included in the subject compositions in amounts of from about 0.01% to about 6% by weight of the total composition.

Sweetening agents may also be employed in the compositions of the present invention in order to make them more palatable. Useful sweetening agents are selected from the group consisting of sucrose, glucose, dextrose, levulose, saccharin salts, thaumatin, aspartame, D-tryptophan, dihydrochalcones, acesulfame salts and cyclamate salts. However, sweetening agents have been found to provide no beneficial effect other than making the taste of the compositions of the present invention more palatable. If present, sweetening agents are generally included in the subject compositions in amounts of from about 0.01% to about 5% by weight of the total composition.

Another optional ingredient of the compositions of the present invention is a humectant. Humectants serve to keep the chewing-gum compositions from hardening upon exposure to air, and to give the compositions a moist feel to the mouth. Certain humectants can also impart desirable sweetness of flavor to the subject compositions. The humectant, on a pure basis, generally comprises up to about 60%, desirably from up to about 40%, by weight of the total composition. Suitable humectants for use in compositions of the present invention are selected from the group consisting of glycerin, sorbitol, xylitol, polyethylene glycol, propylene glycol and mixtures and combinations thereof. Desirably, the humectant will be either sorbitol or glycerin.

Buffering agents are another optional ingredient of the compositions of the present invention. The buffering agents serve to retain the pH of the compositions within the preferred range. The buffering agent generally comprises up to about 10%, desirably from about 0.2% to about 5%, by weight of the total composition. Suitable buffering agents for use in compositions of the present invention include soluble phosphate salts.

Another optional ingredient of the compositions of the present invention is a preservative. Preservatives can be provided in the compositions of the present invention to prevent microbial growth in the compositions. Suitable preservatives include methylparaben, propylparaben, and benzoates. Preservatives generally comprise up to about 5%, preferably from about 0.1% to about 2%, by weight of the total composition.

Binders and thickening agents may also be used in the compositions of the present invention. Useful binders and thickening agents include, for example, carrageenan (e.g., Irish moss, Viscarin TP-5 which is an iota carrageenan), low cellulose derivatives (e.g., hydroxyethyl cellulose, sodium carboxymethyl cellulose, sodium carboxymethyl hydroxypropyl cellulose), carboxyvinyl polymers (carbomers), natural gums (e.g., gum karaya, gum arabic, gum tragacanth), polysaccharide gums (e.g., xanthan gum), fumed silica, and colloidal magnesium aluminum silicate.

Nutrients can also be present in the compositions of the present invention, on condition that they are compatible with each of the ingredients. Useful nutrients include folate, retinoids (Vitamin A), Vitamin C, Vitamin E and zinc. If present, the nutrients generally comprise up to about 10% by weight of the total composition.

The chewing-gum compositions of the present invention may also include coloring agents and/or pigments which are used to provide the composition with a desired color. For example, a spearmint flavored gum may be colored so that it has a green appearance.

In another embodiment of this invention, more than one ingredient selected from the group consisting of an acid neutralizing agent, an anti-gas agent and an acid production inhibitor, and desirably all three ingredients, are formed into a chewable tablet which is supplied integrally with the chewing-gum. By "integral", it is meant that the chewable tablet and the chewing-gum come as one complete unit. Desirably, the chewable tablet will either be encased in the chewing-gum base or encase the chewing-gum base. The concentrations of the ingredients in the tablet will be the same as those described above with those concentrations being based on the total weight of the tablet and the chewing-gum base. The optional ingredients, such as surfactants, flavoring agents, sweetening agents, binders, humectants, thickening agents, buffering agents, preservatives, coloring agents and pigments, can be contained in the gum base, in the tablet or in both the gum base and the tablet. The various ingredients in the chewable tablet will be maintained in tablet form by means of pharmaceutically acceptable carriers. These pharmaceutically acceptable carriers are known to a person of skill in the art.

The compositions of this invention address the five multifactorial etiologies of GERD. First, the efficacy of the anti-reflux mechanism is enhanced by chewing the composition in the upright position allowing gravity to maximize esophageal clearance. Additionally, the anti-reflux mechanism is enhanced by primary peristalsis stimulated by the increased salivary secretions and deglutition. Second, the volume of gastric contents is reduced by the action of the anti-gas agent on gas and the action of the acid production inhibitor which decreases gastric volume. Third, the pH of the gastric fluid is increased by the triple action of the acid production inhibitor, the acid neutralizing effect of the antacid, and the dilutional and neutralizing effect of the salivary bicarbonate. Fourth, the efficiency of the esophageal acid clearance is improved through the stimulatory effect of the composition on the salivary glands promoting peristalsis and decreasing the acid contact time. Finally, by reducing the acid contact time, the tissue resistance of the esophageal mucosa to acid permeation is increased.

By addressing the five multifactorial etiologies of GERD, the compositions of this invention can be used to treat GERD. To treat GERD, a chewing-gum preparation, including a chewing-gum base and more than one ingredient selected from the group consisting of an acid neutralizing agent, an anti-gas agent and an acid production inhibitor, is masticated. Desirably, the chewing-gum preparation will be masticated for a period from about 15 to about 30 minutes and then be removed from the mouth. As stated above, while the preparation is being chewed, the acid neutralizing agent, the anti-gas agent and the acid production inhibitor are absorbed through the buccal mucosa or the gastrointestinal tract. One skilled the art will understand that the chewing-gum preparation can be masticated for shorter or longer periods of time and still be effective. Desirably, the acid neutralizing agent, the anti-gas agent, and the acid production inhibitor are formed into a chewable tablet which is encased in the chewing-gum base.

While certain representative embodiments and details have been presented for purposes of illustrating the invention, it will be apparent to those skilled in the art that various changes, modifications and rearrangements in the compositions disclosed herein may be made without departing from the scope of the invention, which is defined in the appended claims.

What is claimed is:

1. A masticatory for treating the multifactorial etiology of gastroesophageal reflux disease comprising: a chewing-gum base, an acid neutralizing agent, an anti-gas agent, and an acid production inhibitor.

2. The masticatory of claim 1 wherein the acid neutralizing agent is selected from the group consisting of calcium carbonate, magnesium oxide, magnesium hydroxide, magnesium trisilicate, magnesium carbonate, aluminum hydroxide and mixtures thereof.

3. The masticatory of claim 1 wherein the anti-gas agent is simethicone.

4. The masticatory of claim 1 wherein the acid production inhibitor is selected from the group consisting of H-2 receptor antagonists, proton pump inhibitors, their hydrochloride salts, and mixtures thereof.

5. The masticatory of claim 1 comprising, by weight percent of the total composition, from about 1 wt. % to about 50 wt. % of the acid neutralizing agent; from about 0.1 wt. % to about 15 wt. % of the anti-gas agent; from about 0.001 wt. % to about 65 wt. % of the acid production inhibitor; and from about 20 wt. % to about 98 wt. % of the chewing-gum base.

6. The masticatory of claim 5 further comprising a flavoring agent.

7. The masticatory of claim 6 wherein the flavoring agent is selected from the group consisting of menthol, organic acids, oil of cinnamon, oil of wintergreen, oil of peppermint, oil of spearmint, oil of sassafras, and oil of clove.

8. The masticatory of claim 6 further including a sweetening agent.

9. The masticatory of claim 8 wherein the sweetening agent is selected from the group consisting of sucrose, glucose, dextrose, levulose, saccharin salts, thaumatin, aspartame, D-tryptophan, dihydrochalcones, acesulfame salts and cyclamate salts.

10. A chewing-gum composition for the treatment of the multifactorial etiology of gastroesophageal reflux disease comprising: a chewing-gum integral with a chewable tablet, the chewable tablet including an acid neutralizing agent, an anti-gas agent, and an acid production inhibitor.

11. The chewing-gum composition of claim 10 wherein the chewing-gum is contained in the chewable tablet.

12. The chewing-gum composition of claim 10 wherein the chewable tablet is contained in the chewing-gum.

13. The chewing-gum composition of claim 10 wherein the acid neutralizing agent is selected from the group consisting of calcium carbonate, magnesium oxide, magnesium hydroxide, magnesium trisilicate, magnesium carbonate, aluminum hydroxide and mixtures thereof.

14. The chewing-gum composition of claim 10 wherein the anti-gas agent is simethicone.

15. The chewing-gum composition of claim 10 wherein the acid production inhibitor is selected from the group consisting of H-2 receptor antagonists, proton pump inhibitors, their hydrochloride salts, and mixtures thereof.

16. The chewing-gum composition of claim 10 comprising, by weight percent of the total composition, from about 1 wt. % to about 50 wt. % of the acid neutralizing agent; from about 0.1 wt. % to about 15 wt. % of the anti-gas agent; from about 0.001 wt. % to about 65 wt. % of the acid production inhibitor; and from about 20 wt. % to about 98 wt. % of the chewing-gum.

17. The chewing-gum composition of claim 16 further comprising a flavoring agent selected from the group consisting of menthol, organic acids, oil of cinnamon, oil of wintergreen, oil of peppermint, oil of spearmint, oil of sassafras, and oil of clove.

18. The chewing-gum composition of claim 16 further including a sweetening agent selected from the group consisting of sucrose, glucose, dextrose, levulose, saccharin salts, thaumatin, aspartame, D-tryptophan, dihydrochalcones, acesulfame salts and cyclamate salts.

19. A method for treating the multifactorial etiology of gastroesophageal reflux disease comprising the step of masticating a chewing-gum preparation including a gum base, an acid neutralizing agent, an anti-gas agent, and an acid production inhibitor.

20. The method of claim 19 wherein the acid neutralizing agent; the anti-gas agent; and the acid production inhibitor are formed into a chewable tablet which is integral with the chewing-gum base.

* * * * *